United States Patent
Shirasaki et al.

(10) Patent No.: US 7,364,548 B2
(45) Date of Patent: Apr. 29, 2008

(54) ELECTRONIC BLOOD PRESSURE MONITOR AND METHOD OF MANAGING MEASUREMENT DATA OF ELECTRONIC BLOOD PRESSURE MONITOR

(75) Inventors: Osamu Shirasaki, Amagasaki (JP); Takahide Tanaka, Otsu (JP); Kenji Eda, Suita (JP); Kazuomi Kario, 1-1, Midori, Minamikawachi-cho, Kawachi-gun Tochigi (JP) 329-0433

(73) Assignees: Omron Healthcare Co., Ltd., Kyoto (JP); Kazuomi Kario, Tochigi (JP)

( * ) Notice: Subject to any disclaimer, the term of this patent is extended or adjusted under 35 U.S.C. 154(b) by 421 days.

(21) Appl. No.: 11/047,611

(22) Filed: Feb. 2, 2005

(65) Prior Publication Data

US 2005/0171442 A1 Aug. 4, 2005

(30) Foreign Application Priority Data

Feb. 3, 2004 (JP) .............................. 2004-026708

(51) Int. Cl.
*A61B 5/00* (2006.01)

(52) U.S. Cl. ........................ 600/485; 600/490; 600/300

(58) Field of Classification Search ..................... None
See application file for complete search history.

(56) References Cited

U.S. PATENT DOCUMENTS 7,018,335 B2 * 3/2006 Kario et al. ................. 600/485

2003/0060721 A1 * 3/2003 Nakazawa et al. .......... 600/490

FOREIGN PATENT DOCUMENTS

| EP | 0778001 A | 6/1997 |
|---|---|---|
| JP | 11-239566 | 9/1999 |
| JP | 2000-041953 | 2/2000 |
| WO | WO-99/52425 A | 10/1999 |
| WO | WO-02/053024 A | 7/2002 |

OTHER PUBLICATIONS

European Search Report dated Jul. 15, 2005, issued in counterpart foreign application.

* cited by examiner

*Primary Examiner*—Robert L Nasser
(74) *Attorney, Agent, or Firm*—Morrison & Foerster LLP

(57) ABSTRACT

A blood pressure measurement unit measures the blood pressure and a CPU accordingly stores, in a blood pressure storage unit, measurement data as well as time information regarding the time at which the blood pressure is measured. The CPU calculates, as representative measurement data, the average of a plurality of measurement data stored in the blood pressure storage unit and correlated with the time information indicating a time in the range between nine weeks ago and ten weeks ago, correlates the representative measurement data with time information representing the corresponding week and stores the data with the time information in the blood pressure storage unit. At this time, the CPU deletes from the blood pressure storage unit those measurement data based on which the representative measurement data is calculated.

10 Claims, 11 Drawing Sheets

FIG.3A

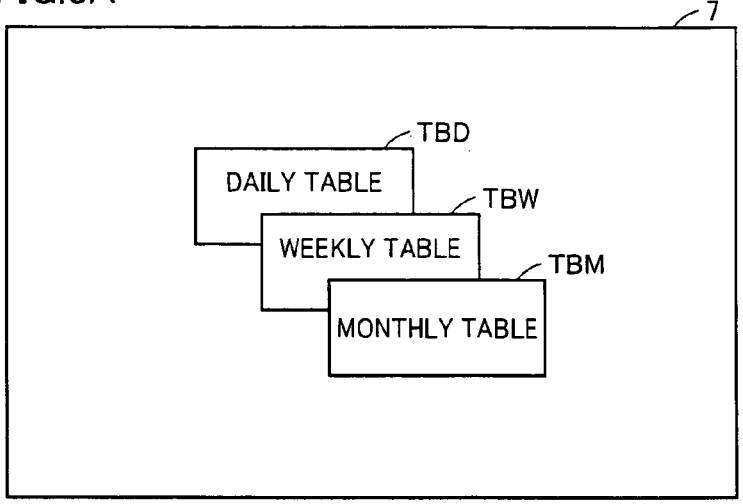

FIG.3B

| | | | | | TBD |
|---|---|---|---|---|---|
| DR— | DT(1):YEAR/MONTH/DATE/HOUR/MINUTE | Sys(1) | Dia(1) | Pr(1) | DBP(1) |
| DR— | DT(2):YEAR/MONTH/DATE/HOUR/MINUTE | Sys(2) | Dia(2) | Pr(2) | DBP(2) |
| DR— | DT(3):YEAR/MONTH/DATE/HOUR/MINUTE | Sys(3) | Dia(3) | Pr(3) | DBP(3) |
| ⋮ | ⋮ | ⋮ | ⋮ | ⋮ | ⋮ |
| DR— | DT(N):YEAR/MONTH/DATE/HOUR/MINUTE | Sys(N) | Dia(N) | Pr(N) | DBP(N) |

FIG.3C

| | | | | | TBW |
|---|---|---|---|---|---|
| WR— | WT(1):03'1/4~1/10 | WSys(1) | WDia(1) | WPr(1) | WBP(1) |
| WR— | WT(2):03'1/11~1/17 | WSys(2) | WDia(2) | WPr(2) | WBP(2) |
| WR— | WT(3):03'1/18~1/24 | WSys(3) | WDia(3) | WPr(3) | WBP(3) |
| ⋮ | ⋮ | ⋮ | ⋮ | ⋮ | ⋮ |
| WR— | WT(N): ⋯ | WSys(N) | WDia(N) | WPr(N) | WBP(N) |

FIG.3D

| | | | | | TBM |
|---|---|---|---|---|---|
| MR— | MT(1):OCTOBER 2003 | MSys(1) | MDia(1) | MPr(1) | MBP(1) |
| MR— | MT(2):NOVEMBER 2003 | MSys(2) | MDia(2) | MPr(2) | MBP(2) |
| MR— | MT(3):DECEMBER 2003 | MSys(3) | MDia(3) | MPr(3) | MBP(3) |
| ⋮ | ⋮ | ⋮ | ⋮ | ⋮ | ⋮ |
| MR— | MT(N): ⋯ | MSys(N) | MDia(N) | MPr(N) | MBP(N) |

ELECTRONIC BLOOD PRESSURE MONITOR AND METHOD OF MANAGING MEASUREMENT DATA OF ELECTRONIC BLOOD PRESSURE MONITOR

BACKGROUND OF THE INVENTION

1. Field of the Invention

The present invention relates to an electronic blood pressure monitor that electronically measures blood pressures and to a method of managing measurement data; In particular, the invention relates to an electronic blood pressure monitor that stores in a memory measurement data taken over a long period of time and to a method of managing the measurement data.

2. Description of the Background Art

With the widespread use of home electronic blood pressure monitors, electronic blood pressure monitors are used for various purposes. This trend is created by the increase of the number of persons who are now in good health and regularly measure the blood pressure at home for the purpose of preventing lifestyle-related diseases, except for those who have conditions diagnosed as hypertension and undergo medical treatment at hospitals. Such a practice would be highly preferable particularly in the current environment of the aging society and tight budgets for social insurance.

There are various blood pressure variation patterns. For example, the blood pressure varies at relatively short intervals in synchronization with breathing, varies depending on physical and mental activities, shows circadian variation (variation in a day), weekly variation (variation in a week), seasonal variation, and variation with age. The circadian variation is generally well-known and given relatively great attention for measurement of the blood pressure. In other words, it has been recommended to measure the blood pressure at the same time every day to obtain necessary information regarding blood-pressure variation and thereby exclude any unnecessary information about the blood-pressure variation. Other types of variations of the blood pressure, however, have been given little attention and consequently an erroneous diagnosis could be made based on a single measurement reflecting these types of variations. For example, the blood pressure varies in a week (weekly variation). In general, the blood pressure of many people is high on weekdays and decreases on weekends. If this weekly variation is ignored and the blood pressure is measured on any weekday of a week and then measured on Saturday or Sunday of another week to compare these measurements of the blood pressure with each other, the comparison could erroneously be made due to overlapping of the weekly variation and the actual variation of the blood pressure. In case of conventional blood pressure monitors, user merely write and keep on a recording sheet measurement values taken each time the blood pressure is measured, and even those monitors having a memory basically show a list of measurement values over a few months at most. Therefore, it is a disadvantage of the conventional blood pressure monitors that observation of the blood pressure in consideration of the above-described blood-pressure variations is difficult.

Moreover, if the blood pressure is monitored for the purpose of preventing lifestyle-related diseases of those who are now in good health as mentioned above, the monitoring period would be a long period of years. Although the issue of how frequently the blood pressure is measured should be considered, a greater memory capacity is necessary for storing measurement values of the blood pressure measured over such a long period of time, resulting in an increase in cost. Technical approaches for solving this problem have been proposed by the applicant of the present application. According to the proposed approaches a device is used that has the function of storing a representative value of measurement data obtained by measuring (detecting) such information about a living body as blood pressure (Japanese Patent Laying-Open No. 2000-41953) and a device is used that displays time-series data of averages of measurement data (Japanese Patent Laying-Open No. 11-239566).

The device of Japanese Patent Laying-Open No. 2000-41953 has a reduced memory capacity achieved by determining a representative value of detected information at predetermined intervals to store the representative value while detecting information about a living body. However, measurement data taken in a predetermined period of time immediately preceding the present time cannot be checked since the data has already been converted into representative data.

The device of Japanese Patent Laying-Open No. 11-239566 merely displays averages for example of blood-pressure values taken in a predetermined period of time on monthly basis for example. Therefore, this device cannot provide finer data about the variation like variation in a week or circadian variation. Under the circumstances, there have been demands for improvements in display manner of measurement data.

SUMMARY OF THE INVENTION

An object of the present invention is to provide an electronic blood pressure monitor capable of efficiently storing recent measurement data as well as measurement data taken a long time ago and to provide a method of managing the measurement data.

Another object of the present invention is to provide an electronic blood pressure monitor capable of storing recent measurement data as well as measurement data taken a long time ago while keeping a smaller memory capacity necessary for storing the measurement data and to provide a method of managing the measurement data.

Still another object of the present invention is to provide an electronic blood pressure monitor capable of storing measurement data keeping necessary information about variation while excluding unnecessary information about the variation and to provide a method of managing the measurement data.

A further object of the present invention is to provide an electronic blood pressure monitor capable of displaying measurement data keeping necessary information about variation while excluding unnecessary information about the variation and to provide a method of managing the measurement data.

According to an aspect of the present invention, an electronic blood pressure monitor includes, for the purpose of achieving the above-described objects: a storage unit for storing provided blood pressure measurement data and time information correlated with the measurement data; a blood pressure measurement unit for measuring blood pressure to provide, to the storage unit, the measurement data and the time information indicating time at which the blood pressure is measured; a representative measurement data calculation unit for calculating representative measurement data representing a plurality of measurement data stored in the storage unit, the plurality of measurement data each correlated with the time information indicating a time in a period between a predetermined first past time threshold and a predetermined second past time threshold relative to the time indicated by the time information correlated with the measurement data; and a representative information supply unit for outputting to the storage unit the representative measurement data calculated by the representative measurement data calculation unit and the time information indicating time reflecting at least one of the first past time threshold and the second past time threshold.

In this way, the time information is constantly checked and, according to the passage of time, the representative data is stored in the storage unit. Here, the representative data represents a plurality of measurement data each correlated with the time information indicating a certain time in the period between the predetermined first past time threshold and the predetermined second past time threshold relative to the time indicated by the time information correlated with the measurement data. Thus, recent measurement data between the present and the period between the predetermined first past time threshold and second past time threshold may be kept in the storage unit as it is. In addition, the measurement data taken in the period between the predetermined first past time threshold and second past time threshold, namely the measurement data taken a predetermined time ago can be stored as the representative data.

Preferably, when the representative measurement data is stored in the storage unit, the plurality of measurement data based on which the representative measurement data calculation unit calculates the representative measurement data are deleted from the storage unit.

Thus, when the representative measurement data is stored in the storage unit, the plurality of measurement data represented by the calculated representative measurement data are erased from the storage unit.

Accordingly, while the capacity of the storage unit necessary for storing measurement data is reduced, measurement data taken a long time ago can be replaced with representative measurement data and stored together with recent measurement data.

Preferably, the length of time between the first past time threshold and the second past time threshold is substantially one week. The representative measurement data representing a plurality of measurement data on the basis of almost one week can thus be calculated.

Preferably, the length of time between the first past time threshold and the second past time threshold is substantially one month. The representative measurement data representing a plurality of measurement data on the basis of almost one month can thus be calculated.

Preferably, the representative measurement data calculation unit calculates, as the representative measurement data, average of the plurality of measurement data. The representative measurement data can thus be calculated by averaging the plurality of measurement data.

Preferably, the time information includes day-of-week information indicating a day of a week. The days of a week are divided into a plurality of day groups each including at least one day of the week, and the representative measurement data calculation unit calculates, for each of the day groups, representative measurement data representing the plurality of measurement data correlated with the time information including the day-of-week information indicating any day included in the day group.

Thus, the representative measurement data representing the measurement data of a predetermined day group is calculated and stored. The stored representative measurement data thus keeps necessary variation information while excluding information concerning weekly variation influenced by the day of the week on which the measurement is taken.

Preferably, the plurality of day groups include a day group including at least one of Monday to Friday. The representative data representing measurement data taken on weekdays is thus calculated and stored to leave necessary variation information while excluding information concerning weekly variation influenced by whether the measurement is taken on weekdays or weekends.

Preferably, the plurality of day groups include a day group including at least one of Saturday and Sunday. The representative data representing measurement data taken on weekends is thus calculated and stored to leave necessary variation information while excluding information concerning weekly variation influenced by whether the measurement is taken on weekdays or weekends.

Furthermore, when those plurality of day groups include a day group including at least one day from Monday to Friday and a day group including at least one of Saturday and Sunday, any difference in stored measurement data between weekdays and weekends can be observed.

Preferably, the time information includes hour/minute information indicating hour/minute at which measurement is performed by the blood pressure measurement unit. One day is divided into a plurality of time periods each defined by a starting hour/minute and an ending hour/minute, and the representative measurement data calculation unit calculates representative measurement data representing the plurality of measurement data correlated with the time information including the hour/minute information indicating any hour/minute included in at least one of the time periods.

In this case, the stored measurement data is the data obtained by taking the measurement in a certain time period everyday. The stored representative measurement data thus keeps necessary variation information while excluding information concerning circadian variation that is variation in blood pressure value even in a day.

Preferably, the second past time threshold is larger than the first past time threshold. The electronic blood pressure monitor further includes a display unit for displaying data, the display unit having a measurement display mode for displaying the measurement data taken when blood pressure is measured by the blood pressure measurement unit and a reading display mode for displaying contents read from the storage unit. The reading display mode has a display mode for displaying the measurement data correlated with the time information indicating a time smaller in value than the first past time threshold, and a display mode displaying the representative measurement data.

Thus, recent measurement data correlated with the time information indicating a smaller value than the first past time threshold can be displayed. Further, representative measurement data representing measurement data taken a long time ago can also be displayed. Accordingly, not only the representative measurement data from which unnecessary information regarding variation is excluded, but also normal measurement data that is not representative data can be displayed for monitoring necessary variation information like weekly variation and circadian variation.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 3A to 3D each show contents of various tables in a blood pressure storage unit according to the first embodiment.

DESCRIPTION OF THE PREFERRED EMBODIMENTS

Embodiments of the present invention are hereinafter described with reference to the drawings.

Structure of Electronic Blood Pressure Monitor

Figure 1:
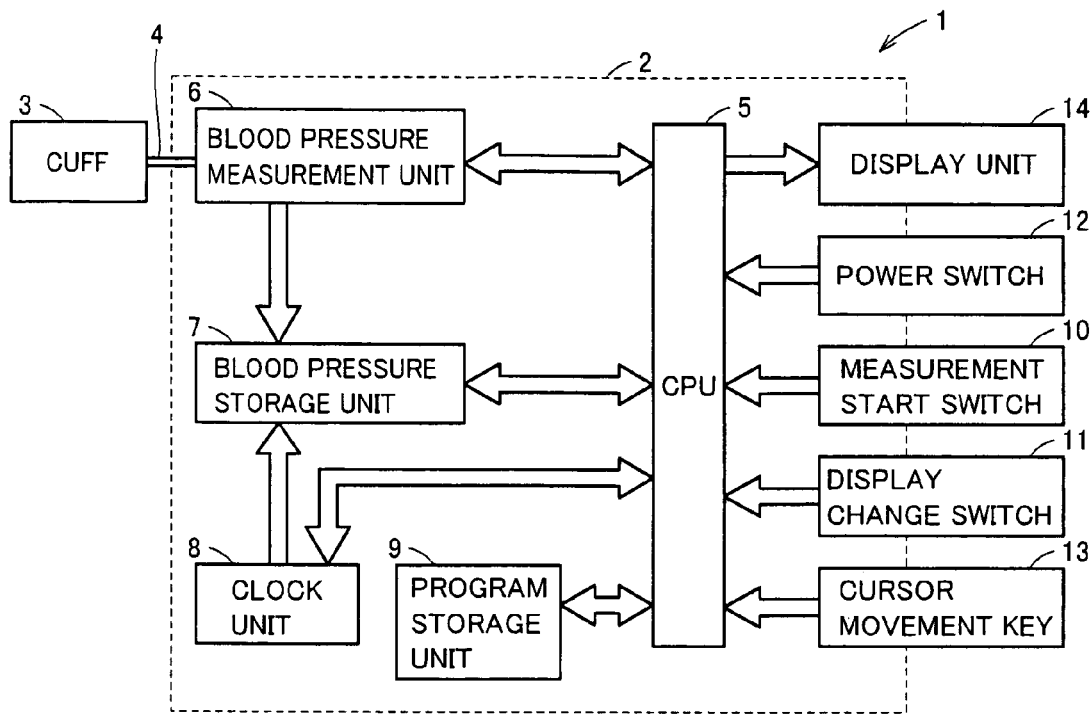
FIG. 1 shows a structure of an electronic blood pressure monitor according to embodiments of the present invention.

FIG. 1 shows a structure of an electronic blood pressure monitor according to the embodiments each of the present invention. Referring to FIG. 1, electronic blood pressure monitor 1 includes a housing 2 indicated by the dotted line in FIG. 1, a cuff 3 provided outside housing 2 and placed on a subject for measuring the blood pressure, and an air tube 4 connecting cuff 3 and a blood pressure measurement unit 6 in housing 2. In housing 2, a CPU (Central Processing Unit) 5 for performing centralized control and management of electronic blood pressure monitor 1 itself, blood pressure measurement unit 6 for measuring the blood pressure, a blood pressure storage unit 7 for storing information concerning the blood pressure that is measurement data, a clock unit 8 for measuring time, a program storage unit 9 for storing various programs and necessary data concerning for example measurement and display of the blood pressure, an operation unit operated for entering various instructions, and a display unit 14 for displaying various information. The operation unit includes a measurement start switch 10 operated for entering an instruction to start measurement of the blood pressure, a display change switch 11 operated for changing the manner of displaying information on display unit 14, a power switch 12 for powering on/off electronic blood pressure monitor 1, and a cursor movement key 13 for operating a displayed cursor on display unit 14. Display change switch 11 is used for making a change between a measurement display mode for showing a measurement value of the blood pressure immediately after the blood pressure is measured and a graph display mode for showing in graph form measurement values in the past that are stored in blood pressure storage unit 7.

Blood pressure measurement unit 6 may operate on any of various principles. Those principles of measurement of the blood pressure that are applicable to blood pressure measurement unit 6 are generally and widely known and thus a description thereof is not given here.

Blood pressure measurement unit 6 is connected to CPU 5 to receive such a signal as blood pressure measurement start control signal from CPU 5 and transmit a measurement value to CPU 5 for displaying the measurement value of the blood pressure on display unit 14. Blood pressure measurement unit 6 is further connected to blood pressure storage unit 7 for storing measurement values. Blood pressure storage unit 7 is connected to clock unit 8 to receive such time information as date, time and day of the week to store the time information together with measurement values of the blood pressure.

Blood pressure storage unit 7 is further connected to CPU 5 for displaying measurement values in the past that are stored as well as the time information on display unit 14.

In addition to the above-described components of electronic blood pressure monitor 1, actually other components like a power supply unit is necessary. The power supply unit to be applied is generally known and is required to have no special performance. Therefore, a description thereof is not given here.

First Embodiment

A concept and a basic process of an operation of calculating representative measurement data by electronic blood pressure monitor 1 are described according to a first embodiment. Although the representative data is calculated herein on a weekly basis, the week may not exactly be one week (seven days) and may be almost one week. Similarly, although the representative data is also calculated herein on a monthly basis, the month may not exactly be one month (31 or 30 days) and may be almost one month.

Description of Principle and Effect

Figure 2:
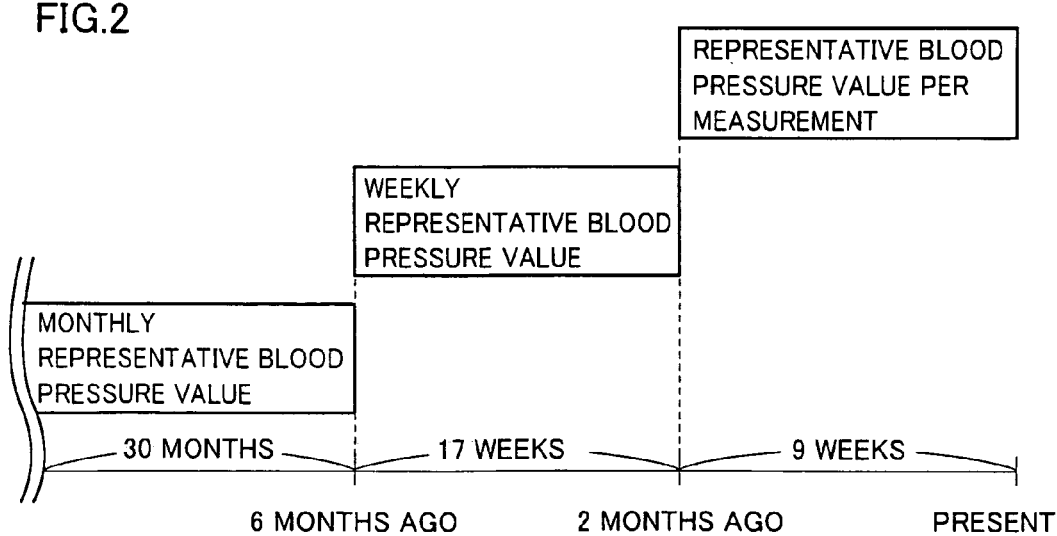
FIG. 2 illustrates a principle and an effect of storage of measurement data according to a first embodiment.

It is supposed here that blood pressure storage unit 7 of electronic blood pressure monitor 1 of a certain user stores such measurement data as values of the blood pressure measured and accumulated over three years. If the user measures the blood pressure four times at regular intervals in a day in consideration of the circadian variation, the number of values of the measurement data is 4380 in total. Since the 4380 values of the measurement data are taken in consideration of the circadian variation, the data includes no unnecessary information regarding the variation while keeping necessary variation information. Here, it is further supposed that values of the blood pressure measured more than two months ago are only necessary to be observed on a weekly basis. Then, such measurement values may be converted into a representative blood pressure value on a weekly basis, for example, an average of each week. Furthermore, it is supposed here that values of the blood pressure measured more than six months ago are only necessary to be observed on a monthly basis. Then, those values may be converted into a representative blood pressure value on a monthly basis, for example, an average of each month. The concept of this method is shown in FIG. 2.

According to this method, recent measurement data for the past two months relative to the present, namely nine weeks, are stored one by one per measurement, measurement data in the period between six months ago and nine weeks ago relative to the present, namely 17 weeks, are converted into a representative value on a weekly basis, and measurement data in the remaining period of more than six months ago, namely 30 months, are converted into a representative value on a monthly basis.

Accordingly, the total of the data to be stored is 299 (4 (times)×7 (days)×9 (weeks)=252)+17 (weeks)+30 (months). As compared with the above-described total of 4380, the total of the data is reduced by 4081, i.e., 93%. This manner of reduction is herein referred to as Reduction Pattern P1.

The blood pressure is generally high on business days and lower on holidays and one may want to separately observe the blood pressure measured on the business days and that measured on holidays. Accordingly, representative blood pressure values may be stored separately depending on the day of the week. For example, a week may be divided into two groups that are a weekday group (at least one of Monday to Friday) and a weekend group (at least one of Saturday and Sunday) and a representative blood pressure value may be calculated and stored for each group. In this case, the number of measurement data over the last nine weeks that are not converted into a representative value is 252 which is identical to that in the above-described example, since the data includes information about the day of the week. The number of representative values on the weekly basis is 34 (17 (weeks)×2 (groups)), and the number of representative values on the monthly basis is 60 (30 (months)×2 (groups)). The number of the measurement data is thus 346 in total. In this case, as compared with the aforementioned total of 4380, the total of the data can be reduced by 4034. In this way, with the weekly variation considered, the measurement data keeping necessary information about the variation while excluding unnecessary variation information can be stored. This manner of reduction is herein referred to as Reduction Pattern P2. Although the representative value is determined here for each of the two groups of the week, a representative value for one of the groups may be determined and the group for which the representative value is determined may be specified so as to exclude information about the variation influenced by the weekly variation.

Moreover, since the blood pressure varies depending on a time period in a day due to the circadian variation, it would also be effective to observe the blood pressure on the time-period basis. For example, 24 hours of a day may be divided into four periods and a representative blood pressure value for each time period may be stored. In this case, the number of measurement data over the last nine weeks that are not converted into a representative value is 252 which is identical to that of the above-described reduction patterns, since the data includes information about the time period of the day. The number of representative values on the weekly basis is 136 (17 (weeks)×2 (groups)×4 (time periods)), and the number of representative values on the monthly basis is 240 (30 (months)×2 (groups)×4 (time periods)). The number of the measurement data is thus 628 in total. In this case, as compared with the aforementioned total of 4380, the total of the measurement data can be reduced by 3752. In this way, with the circadian and weekly variations considered, the measurement data keeping necessary information about the variation while excluding unnecessary variation information can be stored. This manner of reduction is herein referred to as Reduction Pattern P3.

As described above, Reduction Pattern P3 can be used to reduce the number of data to only 628 that still include information about the day of the week and the time period of the day, as compared with the number of data (4380) in the case in which the measurement data is stored one by one per measurement. The data compression effect achieved here corresponds to a reduction of 85%, allowing an increase in memory capacity to be reduced or avoided and thereby significantly reducing the cost. Moreover, when the stored contents are displayed, one can observe the blood pressure without unnecessary blood pressure variation components, namely variation components due to difference in time of measurement. Accordingly, it is a significant medical advantage that inherent variation of the blood pressure can accurately be read from the displayed contents.

Description of Operation

Regarding this embodiment, features of electronic blood pressure monitor 1, namely an operation concerning the storage, calculation and display of data already obtained by measurement with cuff 3 and blood pressure measurement unit 6 (the data is herein simply referred to as measurement data) is described. Then, operations except for the operation concerning the features, for example, an operation of measurement with cuff 3 and blood pressure measurement unit 6 is not described here. It is supposed that the measurement data includes three types of data, namely data Sys representing systolic pressure, data Dia representing diastolic pressure and data Pr representing pulse rate. The types and the number of data included in the measurement data, however, are not limited to the above-specified ones. The pulse rate can be calculated through a known procedure based on information obtained in the process of measuring the blood pressure.

The description here relates to the above-discussed Reduction Pattern P1 providing a reduction of 93%. Further, although the representative value is herein determined as an average of measurement data for relevant time of measurement, the representative value is not limited to the average. For example, the maximum, minimum, or median (average of the maximum and minimum) may be calculated for use as the representative value. If there are upper and lower limits of the blood pressure that should not be exceeded in medical respect, the maximum and minimum values are useful in monitoring whether or not the blood pressure exceeds the limits. If the measurement data is data of blood pressure values, the median is useful in knowing the center of a range of variation of the blood pressure. Since the average tends to be smaller if a relatively large number of measurements are taken when the blood pressure is low, the median may be appropriate for representing the center in some cases.

FIGS. 3A to 3D show exemplary contents of various tables stored in blood pressure storage unit 7. Referring to FIG. 3A, blood pressure storage unit 7 stores a daily table TBD, a weekly table TBW and a monthly table TBM.

Daily table TBD includes, as shown in FIG. 3B, record DR corresponding to each of measurements taken at different times indicated by variable i (i=1, 2, 3, . . . N). As each record DR, time information DT (i) indicating the time of measurement by year, month, date, hour and minute and correlated measurement data DBP (i) are stored. Measurement data DBP (i) includes data Sys (i), Dia (i) and Pr (i) obtained at the measurement time.

Weekly table TBW includes, as shown in FIG. 3C, at least one record WR. As record WR, time information WT (i) specifying one of different weeks indicated by variable i and correlated representative measurement data WBP (i) of the week are stored. Weekly representative measurement data WBP (i) includes data WSys (i), WDia (i) and WPr (i) representing respective averages calculated from data Sys (i), Dia (i) and Pr (i) included in each measurement data DBP (i) correlated with time information DT (i) corresponding to the week.

Monthly table TBM includes, as shown in FIG. 3D, at least one record MR. As record MR, time information MT (i) specifying one of different months indicated by variable i and correlated representative measurement data MBP (i) of the month are stored. Monthly representative measurement data MBP (i) includes data MSys (i), MDia (i) and MPr (i) representing respective averages calculated from data WSys (i), WDia (i) and Wpr (i) included in each measurement data WBP (i) correlated with time information WT (i) corresponding to the month.

Figure 4:
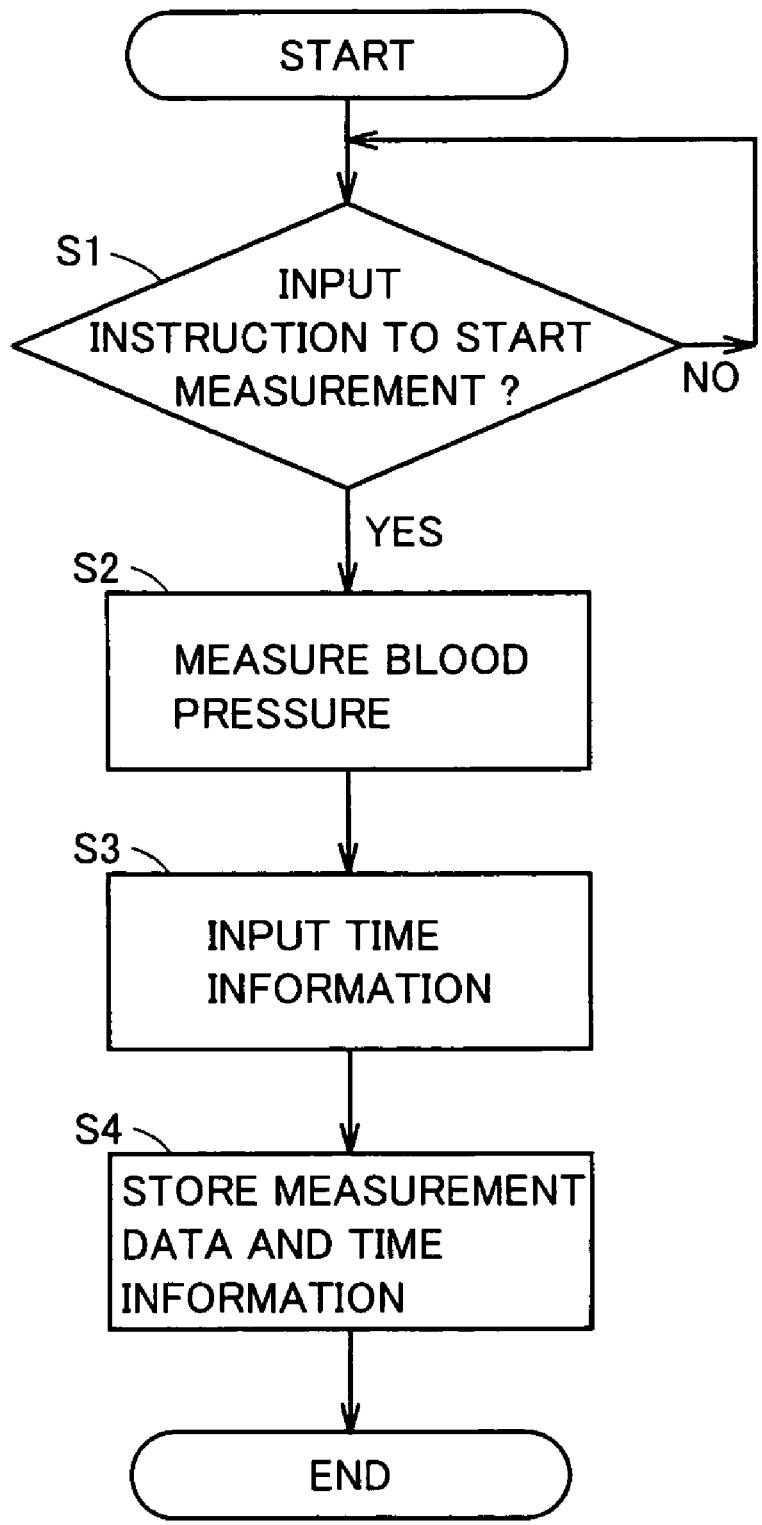
FIG. 4 is a flowchart generally showing a procedure of measuring the blood pressure according to the first embodiment.

FIG. 4 shows a procedure for storing blood pressure measurement data. The procedure is stored in advance as a program in program storage unit 9. CPU 5 reads and executes the program from program storage unit 9.

A subject places cuff 3 on a site of measurement to be ready for measurement of the blood pressure, and then operates measurement start switch 10. When the measurement start switch 10 is operated, an instruction to start measurement is issued to CPU 5 in step S1. Then, in step S2, CPU 5 controls blood pressure measurement unit 6 to measure the blood pressure. In the process of measuring the blood pressure, the pulse rate can also be measured through a known procedure.

After the blood pressure is measured, in step S3, CPU 5 receives time information indicating the current time that is input from clock unit 8. In step S4, the measurement data obtained in step S2 is correlated with the time information input in step S3 to store them as record DR in daily table TBD in blood pressure storage unit 7. The example of the contents of blood pressure storage unit 7 is shown in FIG. 3A.

Although the time information is input after the blood pressure is measured, the time information may be input immediately before the start of measurement of the blood pressure.

Figure 5:
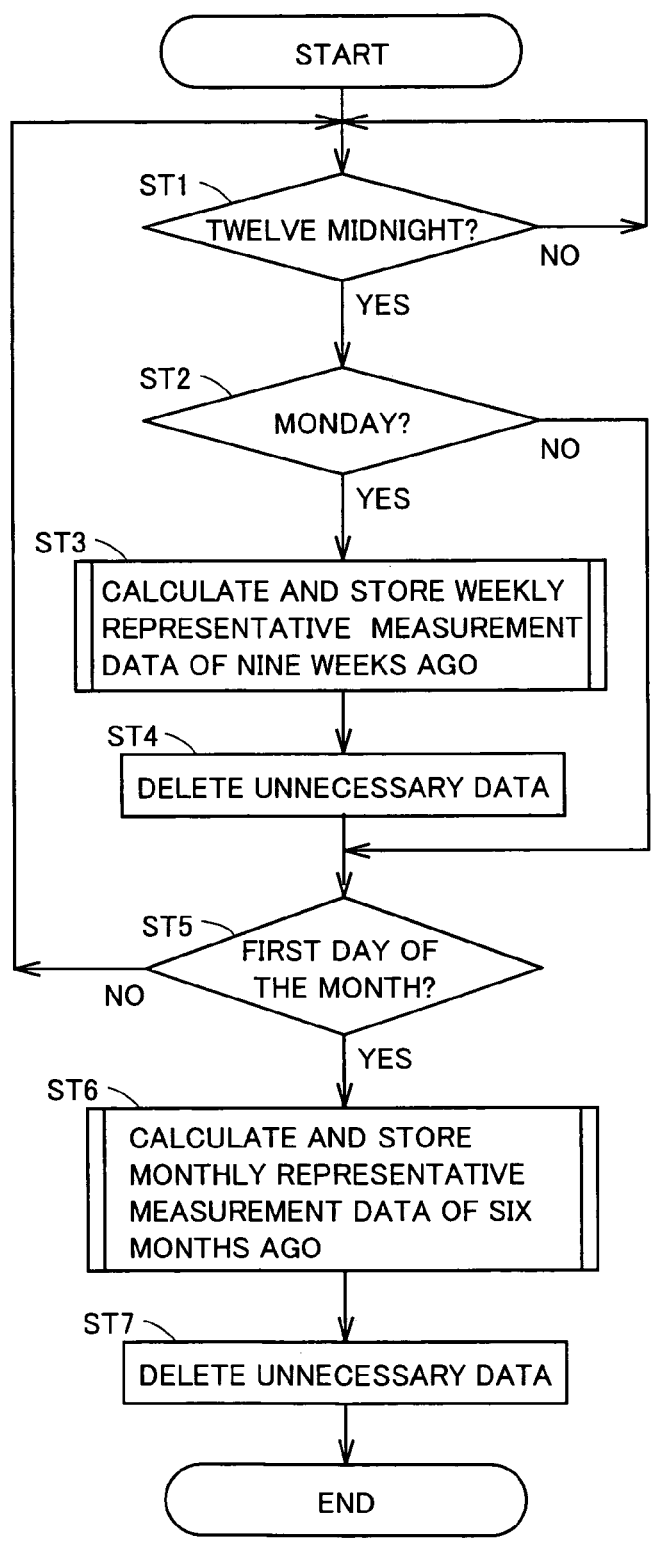
FIG. 5 is a flowchart of a procedure of calculating representative measurement data according to the first embodiment.

FIG. 5 is a flowchart showing a procedure for calculating representative measurement data using electronic blood pressure monitor 1. The flowchart is stored in advance as a program in program storage unit 9 and read and executed by CPU 5.

The representative measurement data is automatically calculated based on the time information indicated by clock unit 8, independently of the manual operation of the user for measuring the blood pressure and displaying the measurement value. Specifically, CPU 5 always sets in operation clock unit 8 in a sleep mode even when the blood pressure is not measured and/or the measurement value is not displayed, and CPU further continues monitoring the time for detecting an instant at which the present time measured by clock unit 8 reaches a specific time (twelve midnight in this embodiment) to carry out the following operation at that instant.

In step ST1 of FIG. 5, whether or not the time is twelve midnight is checked. Namely, this step is performed in the sleep mode of CPU 5.

At twelve midnight, CPU 5 is started in a normal operation mode and step ST2 is performed to detect whether or not the present day is Monday based on the time information indicated by clock unit 8. While Monday is detected in this embodiment since weekly representative measurement data WBP (i) is herein calculated using Monday as the initial day and Sunday as the last day, other days of the week may be used as the initial and last days to calculate the weekly representative measurement data. In this case, the day of the week used as the initial day may be detected.

If the present day is Monday, the process proceeds to the subsequent step ST3 to calculate weekly representative measurement data WBP (i) based on measurement data DBP (i) taken and stored in advance in daily table TBD in the period between nine weeks ago, which is a first past time threshold, and ten weeks ago, which is a second past time threshold, relative to the present day of the week, and the calculated data is stored in weekly table TBW of blood pressure storage unit 7 (this process is detailed hereinlater). Further, in the subsequent step ST4 for deleting data by CPU 5, record DR of measurement data DBP (i) based on which weekly representative measurement data WBP (i) is calculated is deleted from daily table TBD. If the present day is not Monday, the process proceeds to step ST5.

In the subsequent step ST5, it is determined whether or not the present day is the first day of the month. If not, the process returns to step ST1 and the mode of CPU5 changes to the sleep mode. If it is the first day of the month, monthly representative measurement data MBP (i) is calculated based on weekly representative measurement data WBP (i) taken and stored in the period between six months ago, which is a first past time threshold, and seven months ago, which is a second past time threshold, relative to the present day, and the calculated data is stored in monthly table TBM of blood pressure storage unit 7 (this process is detailed hereinlater). Further, in step ST7 for deleting data by CPU 5, record WR of measurement data WBP (i) based on which monthly representative measurement data MBP (i) is calculated is deleted from weekly table TBW.

Calculation of Weekly Representative Measurement Data

Figure 6:
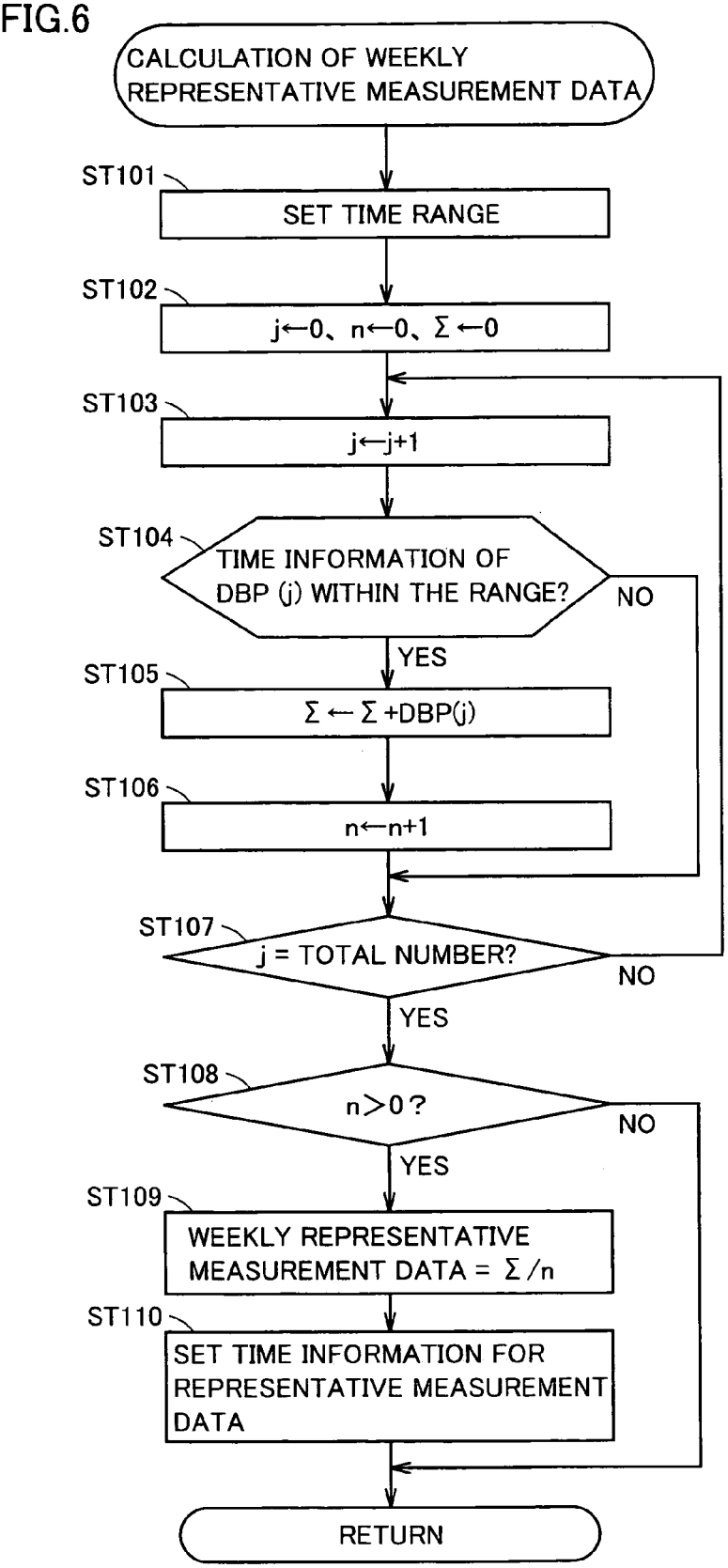
FIG. 6 is a flowchart of a routine of calculating weekly representative measurement data according to the first embodiment.

FIG. 6 shows a flowchart of a routine for calculating weekly representative measurement data in step ST3 of FIG. 5. The flowchart is stored as a program in advance in program storage unit 9 and read and executed by CPU 5.

Control variable j shown in the flowchart of FIG. 6 is used for specifying each of measurement data DBP (i) in daily table TBD, and control variables n and $\Sigma$ are used for counting the total number of measurement data DBP (i) based on which representative measurement data WBP (i) is calculated and the total value (sum). Here, control variable $\Sigma$ represents the sum of each of data Sys (i), data Dia (i) and data Pr (i) included in measurement data DBP (i).

This routine is started to set in step ST101 a range of measurement time (date and time) for which weekly representative measurement data WBP (i) is calculated. Specifically, the set range is the period between nine weeks ago and ten weeks ago relative to the present for example. The range of measurement time may be fixed or arbitrarily set by a user (variable).

In the subsequent step ST102, various control variables are initialized. Specifically, control variables j, n and $\Sigma$ are initialized to zero.

In the subsequent step ST103, the value of control variable j is incremented by one. In step ST104, CPU 5 determines whether or not time information (detected year, month, date, hour, minute) DT (i) correlated with measurement data DBP (j) in daily table TBD is included in the above-described range. If so, in step ST105, the value of data Sys (j), the value of data Dia (j) and the value of data Pr (j) included in this measurement data DBP (j) are each added to a corresponding value of control variable $\Sigma$. Then, in step ST106, control variable n is incremented by one. If the time information is out of the set range, the routine proceeds to step ST107.

In the following step ST107, it is determined whether or not the value of control variable j indicating measurement data DBP (i) to be processed at this time reaches the total number of data stored in daily table TBD, namely whether the value indicates measurement data DBP (i) registered lastly in daily table TBD. If the value is less than the total number of the data, the routine returns to step ST103 to repeat the subsequent steps similarly. If the value indicates the total number of the data, the routine proceeds to the following step ST108.

In step ST108, CPU 5 determines whether or not a condition n>0 is satisfied, namely whether or not the number of measurement data DBP (i) added to control variable Σ representing the sum is more than zero. If the number is zero, it is meant that measurement data DBP (i) within the aforementioned time range is not included in daily table TBD. Then, the following steps are skipped and this routine is ended.

If the condition n>0 is satisfied and the number of measurement data DBP (i) added to control variable Σ is one or more than one, CPU 5 calculates (Σ/n) to determine weekly representative measurement data WBP (i) in step ST109. Here, calculation of (Σ/n) means division, by the value of control variable n, each of the sum of data Sys (i), the sum of data Dia (i) and the sum of data Pr (i) represented by control variable Σ. Thus, weekly representative data WBP (i) determined by (Σ/n) includes data WSys (i), data WDia (i) and data WPr (i) representing respective weekly representative values of data Sys (i), data Dia (i) and data Pr (i).

In step ST110 in which CPU 5 provides representative information, CPU 5 newly registers record WR in weekly table TBW. In newly registered record WR, CPU 5 writes (sets) weekly representative measurement data WBP (i) obtained in the above-described manner and new time information WT (i) correlated therewith. This time information WT (i) may be set to indicate or reflect the time of the start or the end (namely nine weeks ago or ten weeks ago) of the time range set in step ST101. For example, the initial date of the week corresponding to nine weeks ago or ten weeks ago may be set.

While weekly representative measurement data WBP (i) is calculated here regardless of time periods in a day in which measurements are taken, weekly representative measurement data may be determined for each of the time periods, for example, for the time periods respectively from 5 to 9, 9 to 12, 12 to 20 and 20 to 22. In this case, weekly table TBW is prepared for each of the different time periods. Then, the procedure shown in FIG. 6 is followed for -measurement data DBP (i) correlated with time information DT (i) of that time period to calculate weekly representative measurement data WBP (i).

After the above-described routine, the main routine shown in FIG. 5 is followed to carry out the operation in step ST4. In step ST4, record DR of measurement data DBP (i) of the number of control variable n added to control variable Σ for calculating weekly representative measurement data WBP (i) is deleted from daily table TBD.

Calculation of Monthly Representative Measurement Data

Figure 7:
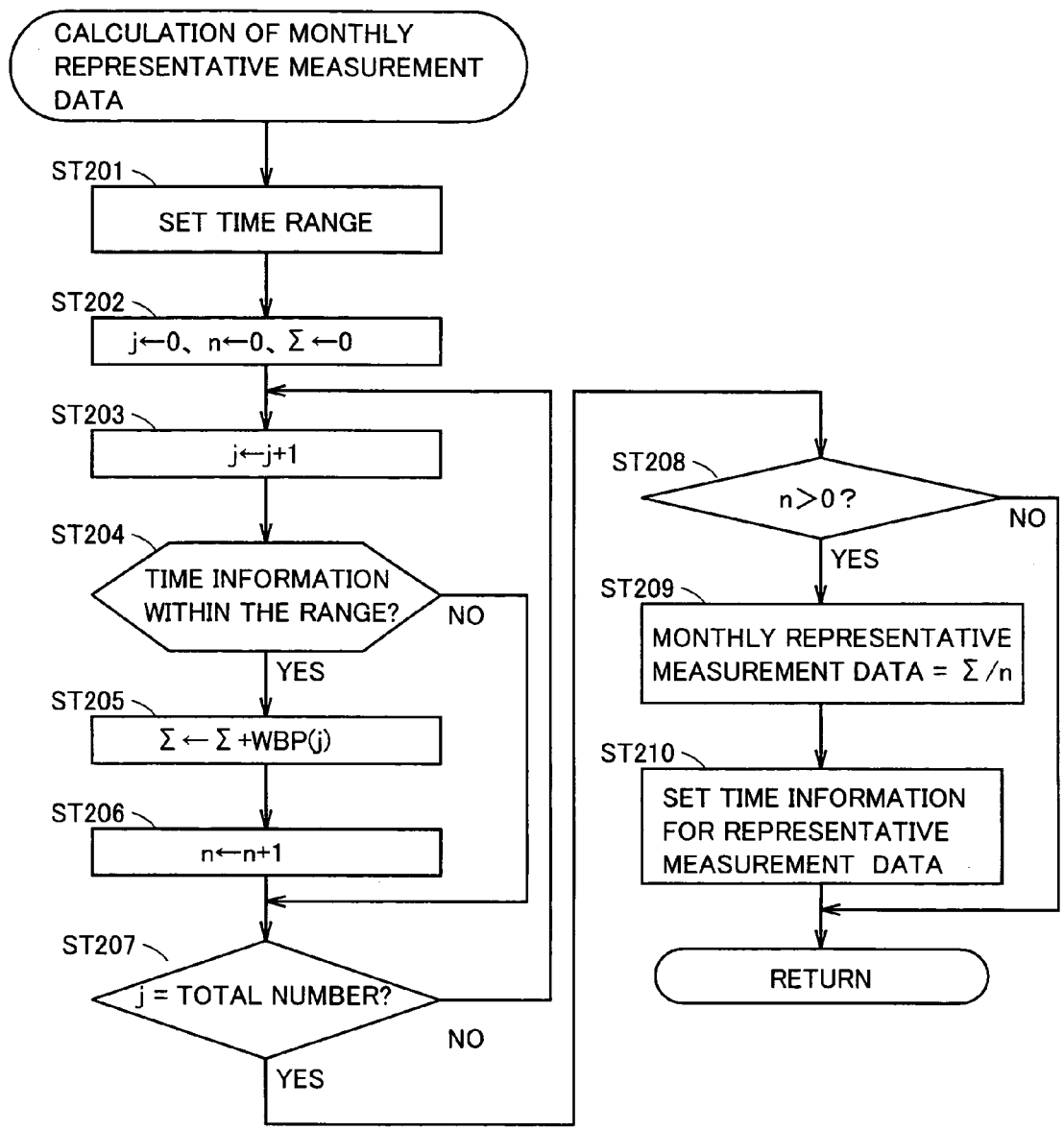
FIG. 7 is a flowchart of a routine of calculating monthly representative measurement data according to the first embodiment.

FIG. 7 shows a flowchart of a routine for calculating monthly representative measurement data in step ST6 of FIG. 5. The flowchart is stored as a program in advance in program storage unit 9 and read and executed by CPU 5.

Control variable j shown in the flowchart of FIG. 7 is used for specifying each of measurement data WBP (i) in weekly table TBW, and control variables n and Σ are used for counting the total number of weekly representative measurement data WBP (i) based on which representative measurement data MBP (i) is calculated and the total value (sum) of the data. Here, control variable Σ represents the sum of each of data WSys (i), data WDia (i) and data WPr (i) included in weekly representative measurement data WBP (i).

This routine is started to set in step ST201 a range of measurement time (date and time) for which monthly representative measurement data MBP (i) is calculated. Specifically, the set range is the period between six months ago and seven months ago. The range of measurement time may be fixed or arbitrarily set by a user (variable).

In the subsequent step ST202, various control variables are initialized. Specifically, control variables j, n and Σ are initialized to zero.

In the subsequent step ST203, the value of control variable j is incremented by one. In step ST204, it is determined whether or not time information (date) WT (i) correlated with weekly representative measurement data WBP (j) in weekly table TBW is included in the above-described range. If so, in step ST205, the value of data WSys (j), the value of data WDia (j) and the value of data WPr (j) included in this weekly representative measurement data WBP (j) are each added to a corresponding value of control variable Σ. Then, in step ST206, control variable n is incremented by one. If the time information is out of the set range in step ST204, the routine proceeds to step ST207.

In the following step ST207, it is determined whether or not the value of control variable j indicating weekly representative measurement data WBP (i) to be processed at this time reaches the total number of data stored in weekly table TBW, namely whether the value indicates weekly representative measurement data WBP (i) registered lastly in weekly table TBW. If the value is less than the total number of the data, the routine returns to step ST203 to repeat the subsequent steps similarly. If the value indicates the total number of the data, the routine proceeds to the following step ST208.

In step ST208, it is determined whether or not a condition n>0 is satisfied, namely whether or not the number of weekly representative measurement data WBP (i) added to control variable Σ representing the sum is more than zero. If the number is zero, it is meant that measurement data WBP (i) within the aforementioned time range is not included in weekly table TBW. Then, the following steps are skipped and this routine is ended.

If the condition n>0 is satisfied and the number of weekly representative measurement data WBP (i) added to control variable Σ is one or more than one, (Σ/n) is calculated to determine monthly representative measurement data MBP (i) in step ST209 by CPU 5. Here, calculation of (Σ/n) means division, by the value of control variable n, each of the sum of data WSys (i), the sum of data WDia (i) and the sum of data WPr (i) represented by control variable Σ. Thus, monthly representative data MBP (i) determined by (Σ/n) includes data MSys (i), data MDia (i) and data MPr (i) representing respective monthly representative values of data Sys (i), data Dia (i) and data Pr (i).

In step ST210 in which CPU 5 provides representative information, CPU 5 newly registers record MR in monthly table TBM. In newly registered record MR, CPU 5 writes (sets) monthly representative measurement data MBP (i) obtained in the above-described manner and new time information T (i) correlated therewith. This time information T (i) may be set to indicate or reflect the time of the start or the end (namely six months ago or seven months ago) of the time range set in step ST201. For example, the initial date of the month corresponding to six months ago or seven months ago may be set.

While monthly representative measurement data MBP (i) is calculated here regardless of time periods in a day in which measurements are taken, monthly representative measurement data may be determined for each of the time periods, for example, for the time periods respectively from 5 to 9, 9 to 12, 12 to 20 and 20 to 22. In this case, monthly table TBM is prepared for each of the different time periods. Then, for each time period, weekly representative measurement data WBP (i) correlated with time information WT (i) corresponding to this time period is specified in weekly table TBW prepared for this time period. The procedure shown in FIG. 7 is followed for the specified weekly representative measurement data WBP (i) to calculate monthly representative measurement data MBP (i).

After the above-described routine, the main routine shown in FIG. 5 is followed to carry out the operation in step ST7. In step ST7, record WR of weekly representative measurement data WBP (i) of control variable n added to control variable Σ for calculating monthly representative measurement data MBP (i) is deleted from weekly table TBW.

As seen from the procedures shown in FIGS. 5 to 7, CPU 5 constantly checks time information provided from clock unit 8 to calculate weekly representative measurement data WBP (i) and monthly representative measurement data MBP (i) according to the passage of time. Thus, for data that is taken a long time ago, representative data is determined and stored in blood pressure storage unit 7 so that blood pressure storage unit 7 stores measurement data in which necessary variation information is kept and from which unnecessary variation information is actively deleted.

Further, each time weekly representative measurement data WBP (i) and monthly representative measurement data MBP (i) are calculated, measurement data DBP (i) and weekly representative measurement data WBP (i) based on which the weekly and monthly representative measurement data are calculated respectively are deleted from corresponding daily table TBD and weekly table TBW. Accordingly, the required capacity of blood pressure storage unit 7 as well as the cost can be reduced.

The foregoing description is applied to Reduction Pattern P1 discussed above. However, the present invention is not limited thereto. Specifically, the invention is similarly applicable to the above-discussed Reduction Pattern P2 or P3 according to which the measurement day of the week or the measurement period of time in a day may be used to calculate and store the representative value of the measurement data. In this case, for measurement data taken a long time ago, representative data correlated with the day of the week or the period of time in the day may be determined and stored. Accordingly, blood pressure storage unit 7 can store measurement data in which necessary variation information is kept and from which unnecessary variation information is actively deleted.

As an alternative calculation of the representative measurement data, an average weighted by the number of days may be calculated. For example, when monthly representative measurement data is to be determined and the first or last week of the month for which the data is determined is less than seven days, weekly representative measurement data for a week having seven days in the month and weekly representative measurement data for a week having less than seven days in that month may be weighted by different factors respectively to determine monthly representative measurement data. In this way, the monthly representative measurement data can accurately be determined.

Second Embodiment

A description is now given below of an operation of reading contents of blood pressure storage unit 7 storing representative measurement data calculated in the above-described manner while displaying the contents on display unit 14.

Figure 8:
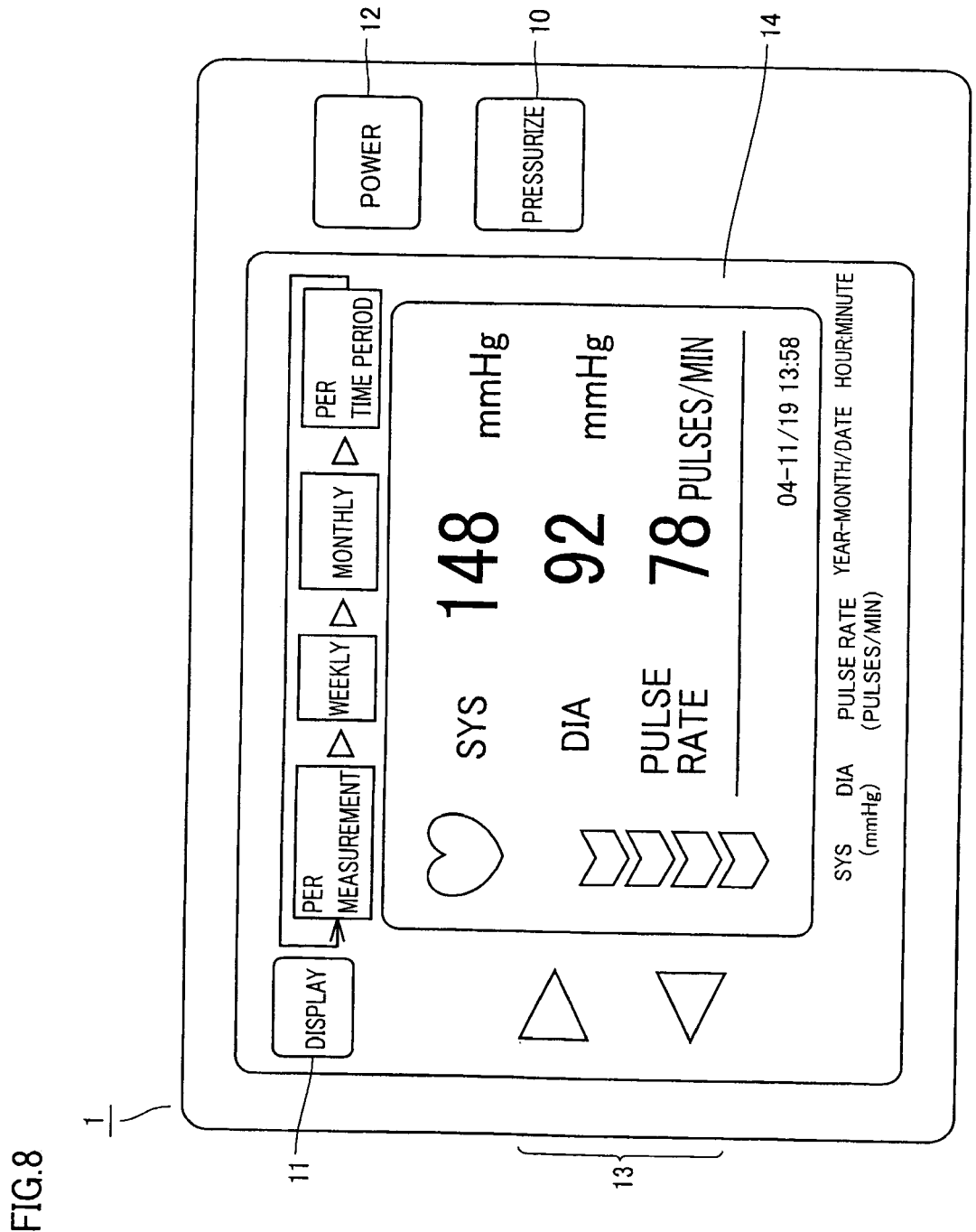
FIG. 8 shows an example of display in a measurement display mode according to a second embodiment.

FIG. 8 shows electronic blood pressure monitor 1 having its housing with a surface on which display unit 14 and the operation unit are provided. On display unit 14, an example of display of measurement data is shown. The measurement data is displayed immediately after the blood pressure is measured to provide the measurement data. Power switch 12 is operated to power electronic blood pressure monitor 1. After powering, measurement start switch 10 is operated to start measurement of the blood pressure. When display change switch 11 is operated while the device is powered, the display mode of display unit 14 is changed between a measurement display mode in which measurement data at the time of measurement by blood pressure measurement unit 6 is displayed and a graph display mode in which contents read from blood pressure storage unit 7 are displayed in graph form. Cursor movement key 13 may be operated to move a cursor for designating any past measurement data indicated on the graph in the graph display mode detailed hereinlater. Display unit 14 maybe formed of a liquid crystal display panel of the dot matrix system for example to display with large characters/numerals, in the measurement display mode as shown in FIG. 8, measurements of the blood pressure and pulse rate obtained immediately after the blood pressure is measured and to display a graph described hereinlater.

FIGS. 9 to 12 show exemplary displays in the graph display mode. In the graph display mode, each time display change switch 11 is pressed, a display mode indicator 15 moves to change the display mode for displaying a graph according to any of the icons ("per measurement," "weekly," "monthly" and "per-time-period") to which the indicator is moved. Thus, display mode indicator 15 can designate any of the per-measurement display mode, weekly display mode, monthly display mode and per-time-period display mode.

Figure 9:
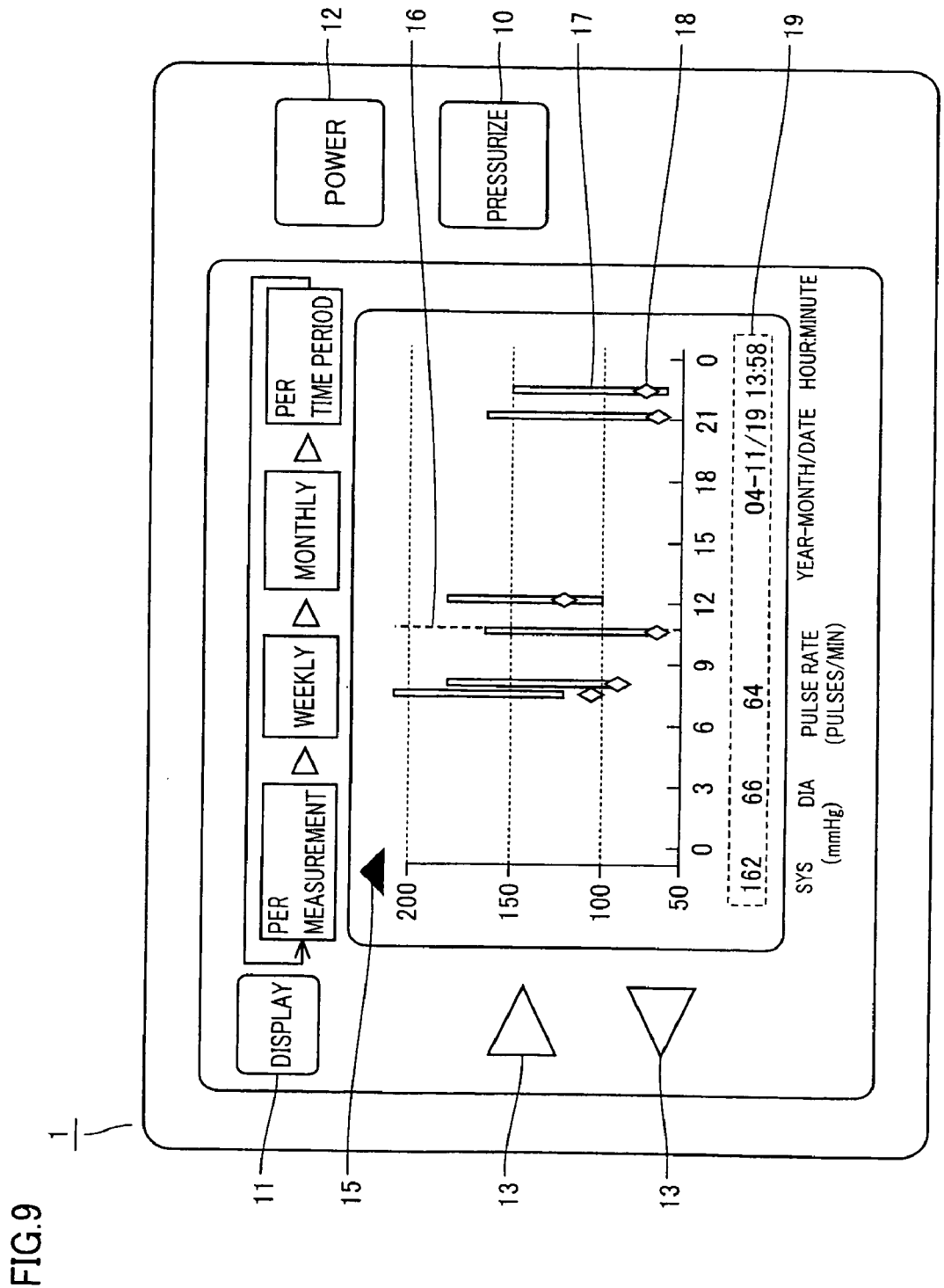
FIG. 9 shows an example of display in a graph display mode according to the second embodiment.

Referring to FIG. 9, a graph display mode is displayed by designation of the per-measurement display mode using display mode indicator 15. In FIG. 9, the blood pressure values derived from data Sys and Dia obtained each time the measurement is performed as well as the pulse rate derived from data Pr are displayed. The horizontal axis indicates time of a day (24 hours) and the vertical axis indicates the blood pressure and pulse rate at certain intervals. In the graph, a bar 17 in the vertical direction represents measurement data for a relevant time of measurement. The upper end of the bar represents the systolic pressure (maximum pressure) derived from data Sys indicated by a corresponding coordinate on the vertical axis, and the lower end of the bar represents the diastolic pressure (minimum pressure) derived from data Dia indicated by a corresponding coordinate on the vertical axis. A lozenge mark 18 indicated in relation with each bar represents the pulse rate derived from data Pr. A cursor 16 shown by the vertical dotted line can be moved using cursor movement key 13.

When cursor 16 is moved to be located on target bar 17 (measurement data) to designate this measurement data, respective values of the measurement data, namely blood pressure, pulse rate, and the date and time of the measurement data indicated by cursor 16 are displayed in a bottom area 19 of the screen. The display data in bottom area 19 is changed each time cursor 16 is moved to change measurement data designated by cursor 16.

Although FIG. 9 shows measurement data of the most recent day, the date of measurement to be displayed may be changed. For example, each time a predetermined key is pressed, the date of measurement may be backed or forwarded successively.

Data to be displayed is determined in the following manner. CPU 5 determines which table of blood pressure storage unit 7 is to be searched according to a display mode designated by display mode indicator 15. When the designated display mode is the per-measurement display mode, daily table TBD is searched for. When the designated display mode is the weekly display mode, weekly table TBW is searched for. When the designated display mode is the monthly display mode, monthly table TBM is searched for. In FIG. 9, when the table for search is determined, CPU 5 reads measurement data of the most recent date from daily table TBD to display the data in graph form. When the measurement data is read, correlated time information is also read. Accordingly, the display of bottom area 19 can immediately be updated.

Figure 10:
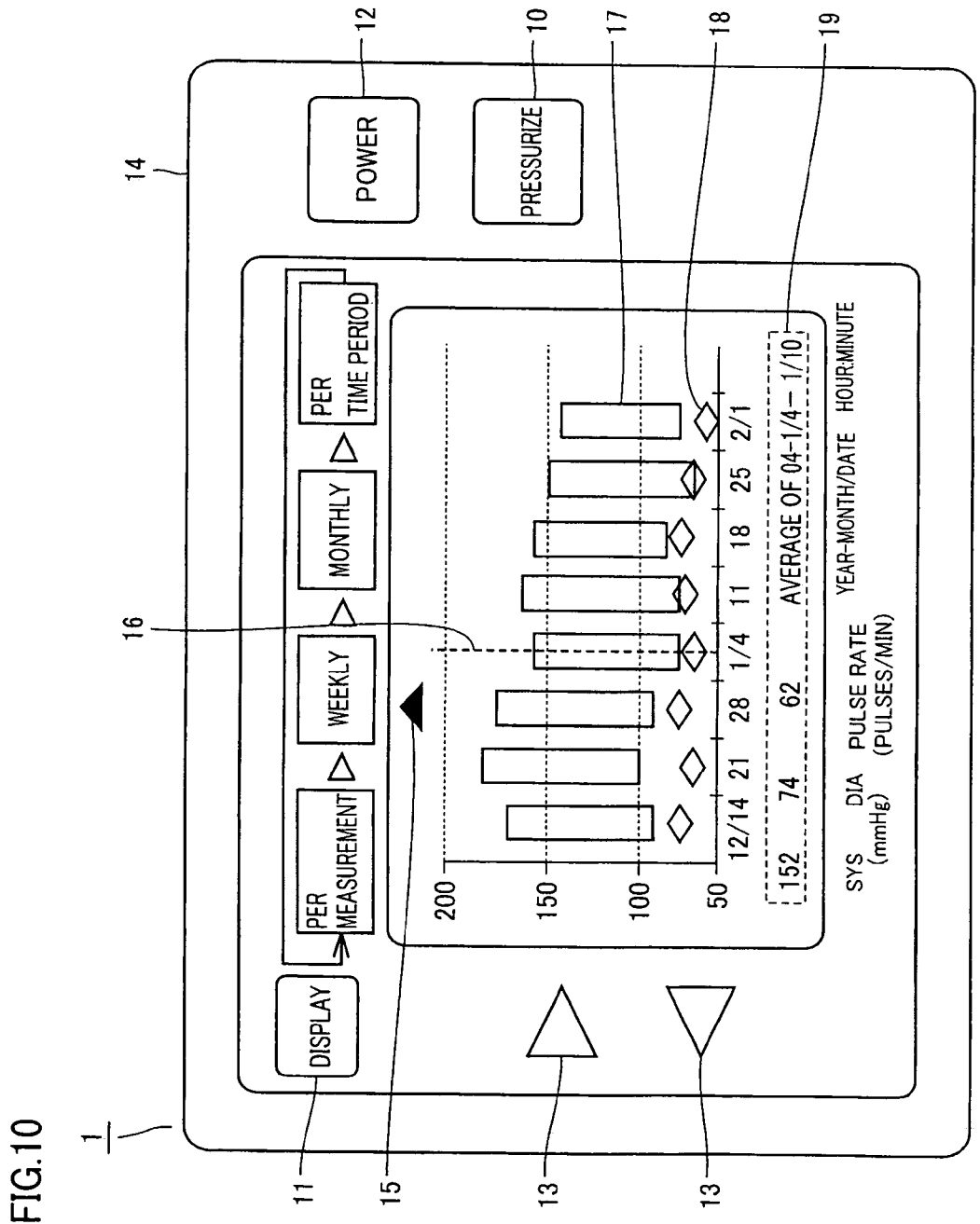
FIG. 10 shows another example of the display in the graph display mode according to the second embodiment.

FIG. 10 shows a manner of displaying a graph when display mode indicator 15 designates the weekly display mode according to the above-described Reduction Pattern P1. The displayed weekly representative measurement data is data for eight weeks read from weekly table TBW. As the per-measurement data display, the values, date and time of the data designated by cursor 16 are indicated in bottom area 19 on the same screen.

Figure 11:
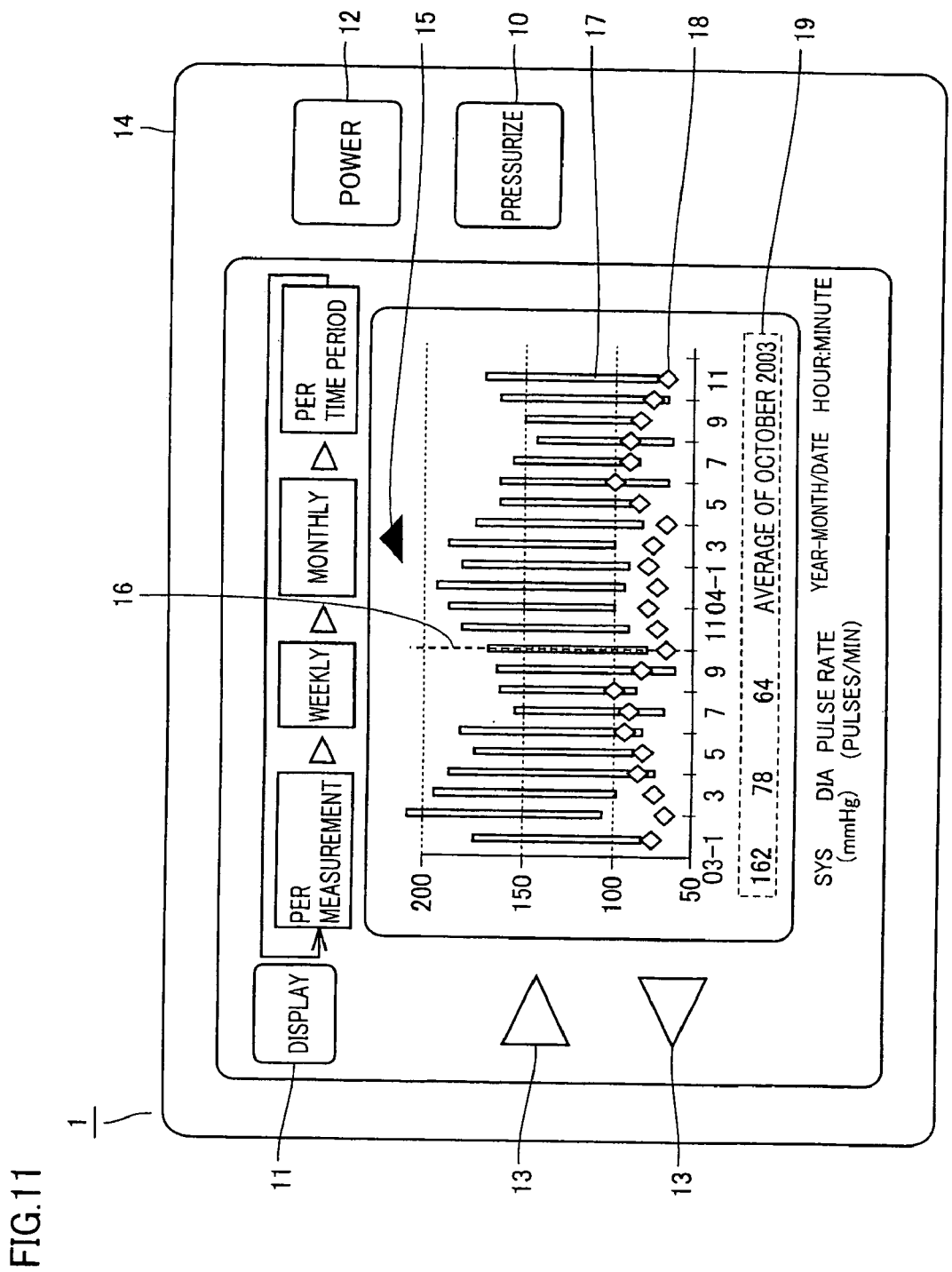
FIG. 11 shows still another example of the display in the graph display mode according to the second embodiment.

FIG. 11 shows a manner of displaying a graph when display mode indicator 15 designates the monthly display mode according to Reduction Pattern P1. The displayed monthly representative measurement data is data for two years (24 months) read from monthly table TBM. As FIGS. 9 and 10, the values, date and time of the data designated by cursor 16 are indicated in bottom area 19 on the same screen.

Figure 12:
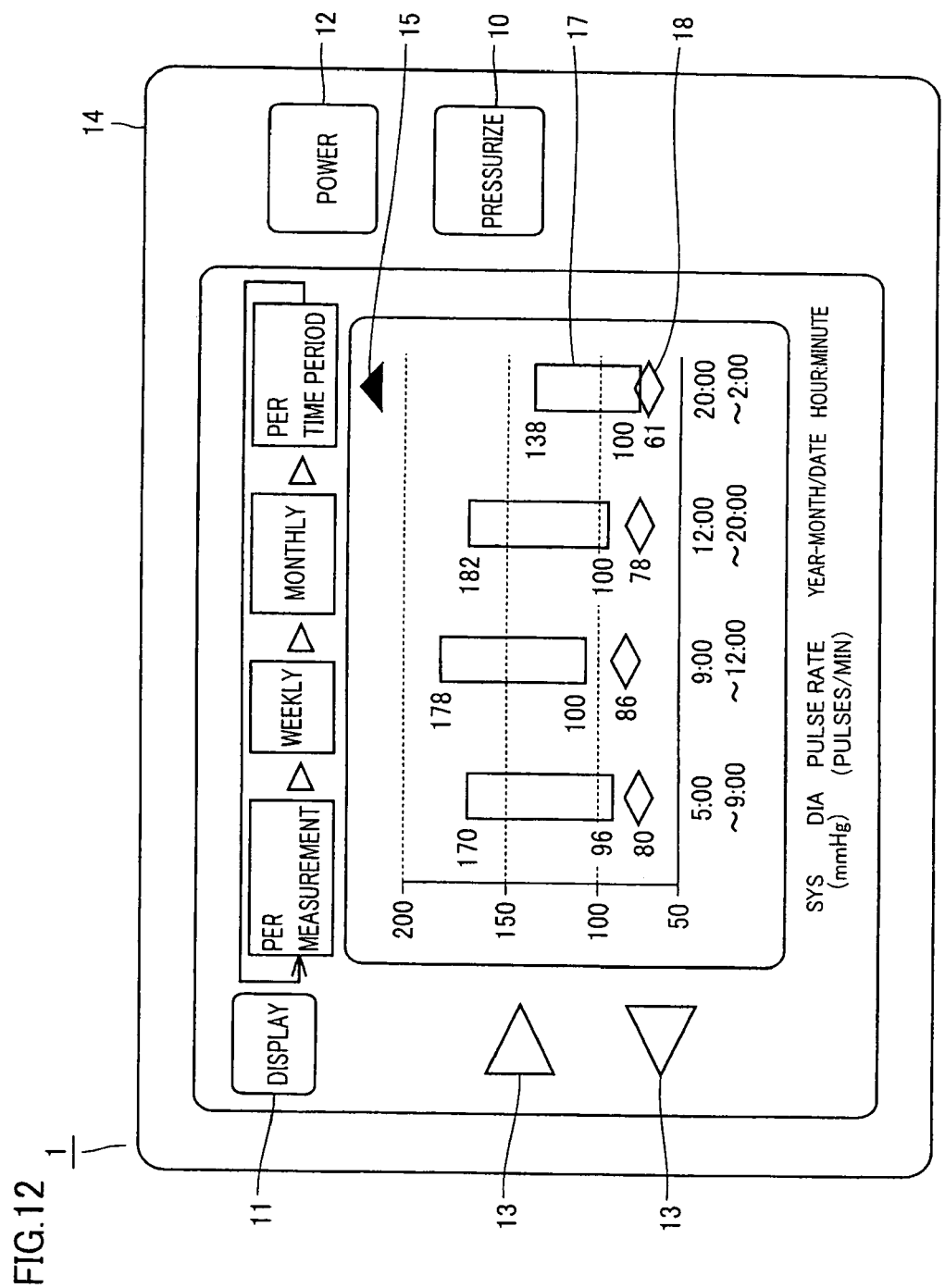
FIG. 12 shows a further example of the display in the graph display mode according to the second embodiment.

Although Reduction Pattern P1 is applied in the display shown in FIGS. 10 and 11 each, any of other reduction patterns may be applied for display. FIG. 12 shows a graph of representative measurement data (average) per time period according to Reduction Pattern P3. A time period is for example one of four time periods into which one day (24 hours) is divided. All of the per-measurement data, weekly representative measurement data and monthly representative measurement data for each time period are displayed. Specifically, display mode indicator 15 is used to designate "per time period" while a key (not shown) is used to make a change between "per measurement," "weekly" and "monthly" and thereby indicate per-measurement data, weekly representative measurement data and monthly representative measurement data correlated with each of the four time periods. In the displayed graph shown in FIG. 12, since there are a relatively smaller number of bars 17 and thus a certain space is left on the display screen and for the advantage of collective display of time, the numerical values of the blood pressure and pulse rate are indicated in relation with bars 17 and marks 18 on the graph.

As heretofore discussed, when measurement data stored in blood pressure storage unit 7 according to the first embodiment is read and displayed, the displayed data includes no unnecessary blood pressure variation components, namely variation components influenced by difference in time of measurement. Accordingly, inherent blood pressure variation can accurately be read by observation of the contents of the display.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic blood pressure monitor comprising:
storage means for storing provided measurement data of blood pressure and time information correlated with the measurement data;
blood pressure measurement means for measuring blood pressure to provide, to said storage means, said measurement data and said time information indicating time at which the blood pressure is measured;
representative measurement data calculation means for calculating representative measurement data representing a plurality of said measurement data stored in said storage means, said plurality of measurement data each correlated with the time information indicating a time in a period between a predetermined first past time threshold and a predetermined second past time threshold earlier than said predetermined first past time threshold relative to the time indicated by said time information correlated with the measurement data;
representative information supply means for outputting to said storage means the representative measurement data calculated by said representative measurement data calculation means and said time information indicating time reflecting at least one of said first past time threshold and said second past time threshold; and
data deletion means for deleting from said storage means, when said representative measurement data is stored in said storage means, said plurality of measurement data based on which said representative measurement data calculation means calculates said representative measurement data,
said storage means retaining, during said deleting by said data deletion means, said measurement data correlated with said time information indicating a time more recent than said first past time threshold,
said representative measurement data calculation means increasing the time period between said first past time threshold and said second past time threshold as the time period increases between said calculation of said representative measurement data and said measurement of said measurement data used to calculate said representative measurement data.

2. The electronic blood pressure monitor according to claim 1, wherein the length of time between said first past time threshold and said second past time threshold is substantially one week.

3. The electronic blood pressure monitor according to claim 1,
wherein the length of time between said first past time threshold and said second past time threshold is substantially one month.

4. The electronic blood pressure monitor according to claim 1,
wherein said representative measurement data calculation means calculates, as said representative measurement data, an average of said plurality of measurement data.

5. The electronic blood pressure monitor according to claim 1, wherein said time information includes hour/minute information indicating hour/minute at which measurement is performed by said blood pressure measurement means, and one day is divided into a plurality of time periods each defined by a starting hour/minute and an ending hour/minute, and said representative measurement data calculation means calculates representative measurement data representing said plurality of measurement data correlated with said time information including said hour/minute information indicating any hour/minute included in at least one of said time periods.

6. The electronic blood pressure monitor according to claim 1, further comprising:

display means for displaying data, said display means having a measurement display mode for displaying said measurement data taken when blood pressure is measured by said blood pressure measurement means and a reading display mode for displaying contents read from said storage means, and said reading display mode has a display mode for displaying said measurement data correlated with said time information indicating a time smaller in value than said first past time threshold, and a display mode displaying said representative measurement data.

7. A method of managing measurement data of an electronic blood pressure monitor comprising the steps of:

storing, in a memory, provided measurement data of blood pressure and time information correlated with the measurement data;

measuring blood pressure to output, to said memory, said measurement data obtained by measuring the blood pressure and said time information indicating time at which the blood pressure is measured;

calculating representative measurement data representing a plurality of said measurement data stored in said memory, said plurality of measurement data each correlated with the time information indicating a time in a period between a predetermined first past time threshold and a predetermined second past time threshold earlier than said predetermined first past time threshold relative to the time indicated by said time information correlated with said measurement data;

supplying representative information for outputting to said memory the representative measurement data calculated by said step of calculating the representative measurement data and said time information indicating time according to at least one of said first past time threshold and said second past time threshold;

deleting from said memory, when said representative measurement data is stored in said memory, said plurality of measurement data based on which said representative measurement data is calculated in said step of calculating the representative measurement data;

retaining in said memory said measurement data correlated with said time information indicating a time more recent than said first past time threshold; and increasing the time period between said first past time threshold and said second past time threshold as the time period increases between said calculating representative measurement data and said measuring measurement data used to calculate said representative measurement data.

8. An electronic blood pressure monitor comprising:

storage means for storing provided measurement data of blood pressure and time information correlated with the measurement data;

blood pressure measurement means for measuring blood pressure to provide, to said storage means, said measurement data and said time information indicating time at which the blood pressure is measured;

representative measurement data calculation means for calculating representative measurement data representing a plurality of said measurement data stored in said storage means, said plurality of measurement data each correlated with the time information indicating a time in a period between a predetermined first past time threshold and a predetermined second past time threshold relative to the time indicated by said time information correlated with the measurement data; and representative information supply means for outputting to said storage means the representative measurement data calculated by said representative measurement data calculation means and said time information indicating time reflecting at least one of said first past time threshold and said second past time threshold, wherein said time information includes day-of-week information indicating a day of a week, and days of a week are divided into a plurality of day groups each including at least one day of the week, and said representative measurement data calculation means calculates, for each of said day groups, representative measurement data representing said plurality of measurement data correlated with said time information including said day-of-week information indicating any day included in said day group.

9. The electronic blood pressure monitor according to claim 8, wherein said plurality of day groups includes a day group including at least one of Monday to Friday.

10. The electronic blood pressure monitor according to claim 8, wherein said plurality of day groups includes a day group including at least one of Saturday and Sunday.

* * * * *